United States Patent [19]

Anderson

[11] Patent Number: 5,278,329
[45] Date of Patent: Jan. 11, 1994

[54] L-FORM 1:1 METAL METHIONINE COMPLEXES

[75] Inventor: Michael D. Anderson, Minnetonka, Minn.

[73] Assignee: Zinpro Corporation, Edina, Minn.

[21] Appl. No.: 839,913

[22] Filed: Feb. 21, 1992

[51] Int. Cl.$^5$ .................... C07F 3/06; C07F 15/02; C07F 11/00; C07F 13/00

[52] U.S. Cl. ........................... 556/50; 556/61; 556/63; 556/134; 556/148; 556/149

[58] Field of Search ............ 556/50, 61, 63, 134, 556/148, 149; 514/492, 494, 502, 505

[56] References Cited

U.S. PATENT DOCUMENTS

| | | | |
|---|---|---|---|
| 3,463,858 | 8/1969 | Anderson | 424/289 |
| 3,647,834 | 3/1972 | Martin | 260/429.9 |
| 3,925,433 | 12/1975 | Abdel-Monem et al. | 260/438.5 R |
| 3,941,818 | 3/1976 | Abdel-Monem | 260/429.9 |
| 3,950,372 | 4/1976 | Abdel-Monem | 260/429 R |
| 4,021,569 | 5/1977 | Abdel-Monem | 424/289 |
| 4,039,681 | 8/1977 | Abdel-Monem | 424/289 |
| 4,067,994 | 1/1978 | Anderson et al. | 424/295 |
| 4,172,072 | 10/1979 | Ashmead | 260/115 |
| 4,216,143 | 8/1980 | Ashmead | 260/113 |
| 4,670,269 | 6/1987 | Abdel-Monem | 426/74 |
| 4,678,854 | 7/1987 | Abdel-Monem | 556/149 |
| 4,764,633 | 8/1988 | Anderson et al. | 556/50 |
| 4,900,561 | 2/1990 | Abdel-Monem et al. | 426/2 |
| 4,948,594 | 8/1990 | Abdel-Monem et al. | 426/2 |
| 4,956,188 | 9/1990 | Anderson | 426/74 |
| 5,061,815 | 10/1991 | Leu | 556/118 |

OTHER PUBLICATIONS

Nakayama et al., Chemical Abstracts 83(13):112369x "Fermentative Production of L-Methionine" JP 50031092, Mar. 27, 1975.

Wada, Chemical Abstracts 82(5):29638t "Production of L-Amino Acids from 2-Hydroxy Acids" (1974).

Nakamori et al, Chemical Abstracts 81(13):76476c "1-- Methionine Production by Ethionine-Resistant Mutants of Brevibacterium" JP 49035580, Apr. 2, 1974.

Nakayama, et al., Chemical Abstracts 75(17):108512f "L-Methionine" DE 2105189, Aug. 12, 1971.

*Primary Examiner*—José G. Dees
*Assistant Examiner*—Porfirio Nazario
*Attorney, Agent, or Firm*—Zarley, McKee, Thomte, Voorhees & Sease

[57] ABSTRACT

Substantially pure 1:1 L-form transition metal methionine complex salts are formed. The preferred transition metals are zinc, chromium, manganese and iron. Salts are formed by reaction with pure L-form methionine. As a result, dosages for supplementation can by way of example be one-half the amount used in raecemic mixtures of salts.

9 Claims, No Drawings

L-FORM 1:1 METAL METHIONINE COMPLEXES

BACKGROUND OF THE INVENTION

The importance of an adequate supply of trace elements zinc, chromium, manganese, iron and of the essential amino acid methionine in the diet of both animals and humans has long been recognized in the literature. Small amounts of trace minerals such as zinc, manganese and iron have also been documented as not only extremely important in dietary function, but for other reasons such as healthy skin, etc. It is common to feed animals such as domestic livestock feed supplements that contain essential amino acids and trace mineral mixes that contain zinc, manganese and iron.

It is also heretofore known that simply choice feeding of free essential amino acids, and conventional inorganic water soluble salts of zinc, chromium, manganese and iron is not the most efficient way for diet supplementation. This is true because neither the amino acid nor the transition metals are in their most bioavailable form in simple choice feeding of conventional simple salts such as zinc chloride, chromium chloride, manganese chloride, and iron chloride.

As a result of the above knowledge, the common assignee of the present application has in the past synthesized and patented certain 1:1 complexes of zinc, chromium, manganese and iron. See for example U.S. Pat. Nos. 3,941,818; 3,924,433: 3,950,372; 4,021,569; 4,067,994. Each of the above patents relate to 1:1 complexes of alpha amino acids, preferably methionine and of transition metals including zinc, chromium, manganese and iron. The complexes shown provided and claimed in the above patents are described as 1:1 complex salts because 1:1 complexes are more water soluble, are more bioavailable, and are more efficiently converted to provide maximum effective body usage of both the transition metal and the amino acid. Such has been demonstrated from data provided in some of the earlier referred to patents of the common assignee.

Each of the above patents describes, prepares and claims raecemic mixtures of the metal methionine complexed salts. That is to say the resulting salt as described is a 1:1 complexed salt which contains within the metal methionine complex, methionine that is a raecemic mixture of the D-form of methionine and the L-form of methionine. In recent times it has been discovered that only the L-form of methionine is bioavailable. In the past it has been believed that the D-form of methionine was converted to the L-form within the body's own biochemical systems. It is now known that this is not the case, and in fact the D-form of methionine is simply passed through and in effect wasted. This pass-through event carried along with it the associated transition metal such that it, too, is hither wasted or less efficiently utilized by the body system.

It has now been discovered that if the complexes are substantially pure L-form complexes, maximized bioavailability of both the transition metal such as zinc, chromium, manganese or iron, and the methionine is accomplished. As a result, dosages can be reduced by for example one-half the amount previously used, and the same bioavailability is achieved. The reason for this is simply that the supplement is in a 100% L-form, and therefore is 100% bioavailable.

Accordingly, it is a primary objective of the present invention to provide substantially pure 1:1 L-form transition metal methionine complexed salts of zinc, chromium, manganese and iron. By preparing only L-form the resulting compounds can be dosed in one-half the amounts now commonly used, and yet the same bioavailability and nutritional supplementation both from the standpoint of the amino acid and from the standpoint of the transition metal are achieved. Costs are reduced.

Another objective of the present invention is to provide a process of preparing substantially pure 1:1 L-form complexes of methionine with zinc, chromium, manganese and iron.

Another important objective of the present invention is to provide compositions for supplementation of diets of animals and humans which can be dosed up to 50% of the levels of the complexes previously known, and yet achieve the same levels of assimilation of zinc, chromium, manganese and iron and methionine into the body systems of the animal, as the earlier used higher doses of raecemic mixtures.

The method of accomplishing these and other objects will become apparent from the following description of the invention.

SUMMARY OF THE INVENTION

This invention relates to novel substantially pure 1:1 L-form transition metal methionine complexed salts of the formula:

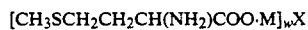

$$[CH_3SCH_2CH_2CH(NH_2)COO \cdot M]_w X$$

wherein M is a transition metal selected from the group consisting of zinc, chromium, manganese and iron; X is a water soluble anion; and W is an integer that balances the anionic charge of X. These compounds are all L-form complexes, and as a result provide both the transition metals and the methionine in a form which is readily absorbed, distributed and utilized within the biochemical system of the animal in the most efficient manner. The compounds therefore function as most economical and efficient, highly bioavailable sources of both the amino acid and the transition metals.

DETAILED DESCRIPTION OF THE INVENTION

A detailed description of preparation of 1:1 metal ion methionine complexes salts need not be described herein, except to the extent that the processing to provide substantially pure 1:1 L-form salts differs from the processing described in the common assignee's previous patents to prepare raecemic mixtures. However, it may be worthy of mention of certain of the essential process features. First, it is important to note that the compounds of the invention are isolatable in solid form. They are also stable and water soluble. In addition, the compounds are 1:1 complexes, because the 1:1 complexes are the most useful. They are the most useful in that the 1:1 complexes have the desired stability, they effectively hold the transition metal in the complex with the amino acid, but do not so strongly attach to the metal that it is not absorbed. They provide both the metal and the methionine in an easily processible, stable form with water solubility, in contrast with 2:1 salts, which are normally not soluble. 1:1 complex salts are achieved by maintaining the pH at 7 or less, preferably on the acid side, and preferably within the range of 2 to 6.

In accordance with the process of the present invention, one obtains substantially pure 1:1 L-form complexes by running reactions as identically described in the above-referred to, commonly assigned patents for each of zinc, chromium, manganese and iron methionine complexes. There is only one important difference. The important difference is that the methionine used cannot be a DL raecemic mixture, as in the earlier patents, but that it must have the L-form separated from the D-form of methionine and only the L-form is used. As a result, since only L-form methionine is used in the reactions, only L-form transition metal complex salts are formed. Substantially pure, that is nearly 100% L-form methionine is commercially available. Generally, the L-form can be obtained from fermentation procedures. See, for example *Chemical Abstracts* 83(13):112369x, which describes fermentive production of L-methionine. In this 1975 Japanese publication, L-methionine was produced by either Pseudomonas, Achromobacter, or Protaminobacter which assimilates MeOH when cultured on a MeOH medium. Thus, Protaminobacter candidus EN-2 (FERM-P 2160), an ethionine resisting mutant, was cultured on a medium (pH 7.2) contg. $(NH_4)_2SO_4$ 7, urea 1.5, $KH_2PO_4$ 2, $K_2HPO_4$ 7, $MgSO_4.7H_2O$ 0.5, yeast ext. 1, and $CaCO_3$ 20 g, plus $FeSO_4.7H_2O$ 10, $MnSO_4.45H_2O$ 8, thiamine-HCl 1, and phenol red 10 mg, plus biotin 10 .mu.g, and MeOH 20 ml at 30° for 67 hr. MeOH was added after 16, 24, and 40 hr of cultivation at 1, 2, and 2%, resp. Prodn. of L-methionine was 92 mg/l. The culture liq. (2 l.) was added with 40 g $CaCl_22H_2O$ and the resulting ppt. was removed by centrifugation. The supernantant was concd. under reduced pressure and the resulting ppt. was removed by centrifugation. The supernatant (45 ml) was charged on a column of Diaion SK-1 (H+) and the L-methionine adsorbed was eluted with 0.3N $NH_4OH$ and crystd. from MEOH yielding 85 mg.

Other literature reports production of L-methionine by strains of bacteria, see for example *Chemical Abstracts* 82(5):29638t entitled "Production of L-Amino Acids From 2-Hydroxyacids". See also, *Chemical Abstracts* 81(13):76476c entitled "1-Methionine Production By Ethionine Resisted Mutants of Brevibacterium". In addition, in *Chemical Abstracts* at CA75(17):108512f, L-methionine itself is described as useful in feed, as a lipotropic agent, or in the treatment of liver diseases of animals, and indicates that L-methionine itself was prepared by fermentation with a corynebacterium strain resistant to alpha methyl methionine. In addition, enzymatic synthesis of L-amino acids such as methionine is described in a publication of Leuchtenberger in the *European Congress of Biotechnology* (Vol. 4701-11), the author is a corporate affiliate of Degussa AG, a firm from which methionine is readily available. This article generally describes the enzymatic synthesis of L-amino acids from prochiral precursors as a favored reaction due to the direct formation of the desired stereospecific form free from the deisomer.

To summarize, L-methionine itself is also commercially available from firms such as Degussa AG. It can be prepared by fermentation processing using bacterium known to produce only L-form methionine, it can be prepared by resolving DL mixtures of amino acid derivatives by hydrolytic enzymes from prochiral precursors, and it can be resolved from raecemic mixtures by other more conventional chemical resolution techniques, if desired.

The following examples are offered to illustrate the formation of substantially pure 1:1 L-form zinc, chromium, manganese and iron complexes with methionine. As used herein, the phrase "substantially pure" refers to having the vast majority of the complexed salt in the L-form. Generally, this is 90% or above and most commonly nearly 100%. It is to be noted in the examples as illustrated the compounds are all isolated from solution, are indicated as stable, are available as water soluble solids, and are all easily prepared, easily usable and processible 1:1 L-form complex salts. In each, the L-form methionine was obtained from Degussa, AG, and was listed as 100% L-form.

EXAMPLE 1

Twenty-eight pounds of hydrated zinc sulfate ($ZnSO_4.H_2O$) was added to 65 pounds of hot water (200° F.). This mixture was stirred until the zinc sulfate had completely dissolved. Next, 22 pounds of pure L-methionine was added under continuous stirring. This hot solution was stirred for aproximately 10 minutes and the temperature of the solution was heated to maintain 200° F. The solution was spray dried using conventional techniques. A dry, free-flowing powder was recovered and analyzed for zinc and methionine. Results showed 20.51% zinc and 44.4% methionine.

EXAMPLE 2 (prophetic)

Hydrated zinc sulphate ($ZNSO.7HO$, 57.5 g 0.2 mol) and L-methionine (29.84 g, 0.2 mol) are mixed thoroughly in an evaporating dish. The mixture is heated on a steam bath to form a paste. Heating is continued for 60 minutes and the paste is transferred into a hot air oven and dried at 90° C. for 20 hours. The resulting product weighed 63.3 g. Quantitative analysis will reveal the product is comprised of 20.37% zinc and 46.5% L-methionine. This indicates a proper ratio of zinc to L-methionine for a 1:1 complex of zinc methionine. Further analysis by infrared analysis and titration curve analysis will indicate the presence of zinc methionine acid sulphate as per the previous example. The product is a dry, free-flowing powder.

While the paste of this example is hot air oven dried, other preparations can be prepared where the resulting solutions are spray-dried in a spray dryer at a temperature of about 400° F. to yield a dry free-flowing powder.

EXAMPLE 3 (prophetic)

Zinc chloride ($ZnCl_2$, 68.0 g, 0.5 mol) is dissolved in water (68.0 g) and the solution is heated to 90° C. L-methionine (74,bg, 0.5 mol) is added and the temperature is kept at 90° C. for one hour to provide zinc methionine chloride solution. The product will contain 21.2% zinc and 53.9% L-methionine. Quantitative and instrumental analysis as previously described will reveal the presence of a 1:1 complex salt of zinc methionine chloride.

EXAMPLE 4 (prophetic)

L-methionine (74.6 g, 0.5 mol) is dissolved in a 165 ml of 6.08N N hydrochloric acid and zinc oxide (40.65 g) is added. The mixture is heated at 90° C. for one hour to provide zinc methionine chloride solution. The product will contain 19.9% zinc and 44.0% L-methionine. The presence of zinc methionine chloride is confirmed by quantitative and instrumental analysis.

EXAMPLE 5 (prophetic)

(Preparation of 1:1 Manganese Methionine Acid Sulphate

L-methionine (1.49 grams — 0.01 moles) is dissolved in about 70 milliliters of distilled water which is being warmed on a steam bath. The dissolved solution is then cooled. Manganese sulphate monohydrate (1.69 grams — 0.01 moles) is dissolved in about 15 milliliters of warm water and is then added to the previously described methionine solution.

The mixture is warmed on a steam bath and most of the water is removed over a rotary evaporator operating under high vacuum. Much of the water distilled at the bath temperature of between 48° and 55° C.

The residue obtained is dissolved in a minimum amount of hot water that would dissolve the residue and is thereafter filtered hot. To the filtrate is added absolute ethyl alcohol until turbidity is noted. It is then cooled in a freezer overnight.

A white granular residue of solid crystalline material is obtained. This is filtered and dried to provide a dry product weighing 2.2 grams. The melting point is determined and found to be between 244° and 254° C. The sample is then dried over benzene (boiling under vacuum) overnight. The melting point is taken again and found to be 251° to 252° C.

The sample is analyzed by infrared analysis, methionine analysis and quantitative analysis for carbon, hydrogen, nitrogen and manganese. Infrared analysis will show the absence of a strong peak at 2100 reciprocal centimeters, which is the characteristic peak for L-methionine. The different peak structures of the product from the peak structures of the reactants will indicate the formation of 1:1 manganese methionine acid sulphate. Quantitative analysis will show the following:

| Theoretical Amount | Found Amount |
|---|---|
| 49.94% methionine | 51.78% methionine (average) |
| 18.3% manganese | 14.35% manganese (average) |
| 20.0% carbon | 21.7% carbon |
| 3.69% hydrogen | 4.63% hydrogen |
| 4.66% nitrogen | 4.71% nitrogen |

The close parallel between the quantitative analysis theoretical amounts and actual found amounts, the infrared analysis, and the differing melting point characteristics, all indicate the presence of desired compound.

The resulting 1:1 manganese methionine acid sulphate is a white crystalline material. It is readily soluble in water at a ratio of 1 gram in 5 milliliters of water at 15° C. and the solution is stable on standing. The product is readily soluble in both simulated gastric juice and simulated intestinal juice. These solubility characteristics are to be contrasted with the slow dissolution of either manganese sulphate or L-methionine under similar conditions in water.

EXAMPLE 6 (prophetic)

1:1 Ferric Methionine Acid Sulfate

Ferrous sulfate ($FeSO_4 \cdot 7 H_2O$, 27.8 g, 0.1 mole) is mixed with water (5.0 g) and concentrated sulfuric acid (5.1 g). The mixture is thoroughly mixed and treated dropwise with hydrogen peroxide (30% solution, 10.5 g). The addition of hydrogen peroxide will result in rise in the temperature of the solution and the production of gases. The green color of the ferrous sulfate solution will change to a reddish brown by the addition of $H_2O_2$. The hot solution is treated with L-methionine (14.9 g) to give a deep reddish clear solution. The solution is concentrated under reduced pressure to 75% its weight and is then spread in a thin film on glass plate and heated in an oven at 85° C. for 30 minutes. The dry mass obtained is pulverized to provide a deep red powder of the ferric methionine sulfate.

EXAMPLE 7 (prophetic)

1:1 Chromium Methionine Sulfate

Two grams of chromium plus 6 oxide (0.02 mol) is reacted with 0.03 moles of sulphuric acid in the presence of 0.04 moles of ethyl alcohol. The chromium plus 6 oxide is reduced to chromium plus 3 sulphate. The reaction mixture is heated and boiled until the solution turns green and no odor of acctaldehyde is given off. Thereafter 2.98 grams of L methionine is added and the mixture is heated on a steam bath until a dark green colored paste forms. The mixture is dried in a hot air oven and instrumental, and quantitative analysis as previously described reveals the presence of a 1:1 L-form complex chromium methionine sulphate salt.

EXAMPLE 8

1:1 zinc (methionine DL mixture) was tested for bioavailability. The test showed that the zinc was available at about 200% level in comparison to zinc from zinc sulfate. On the otherhand the test showed DL methionine bioavailability at only about 60% in comparison to baby chicks fed DL methionine not in the complex. This test led the inventor to conclude L-form would substantially increase the methionine availability. Bioavailability testing of the product of example is now occuring.

EXAMPLE 9

Transport of Zinc Methionine Complexes Across Human Epithelial Cells

A cell culture model was used to determine the transport of zinc d-methionine sulfate and zinc l-methionine sulfate across epithelial cells. A cell line originating from human colon cancer (Caco-2) was grown in a culture media. The cells form a continuous layer with no, or very few, gaps between cells. Substances added at one side of the cell layer is transported across the epithelia cell layer by mechanisms similar to those operating in vivo.

Zinc d-methionine sulfate was not transported from one side of the membrane to the other. Zinc l-methionine sulfate was transported across the membrane. Similarly, d-methionine was not transported across the membrane while l-methionine was transported freely. These results indicate that these amino acids are transported across epithelial cells by a specialized transport system. This system is enantiospecific for the naturally occurring l-methionine. Further, it appears that the zinc methionine sulfate complexes are transported across the epithelial membrane by the same transport system for the free amino acids. Since zinc d l-methionine sulfate is a mixture of equal amounts of zinc d-methionine sulfate and zinc l-methionine sulfate, it is safe to conclude that only zinc l-methionine sulfate in this mixture will be transported across the epithelial membrane and biologically utilized.

What is claimed is:

1. Substantially pure 1:1 L-form transition metal methionine complexed salts of the formula:

$$[CH_3SCH_2CH_2CH(NH_2)COO\ M]_w X$$

wherein M is a metal selected from the group consisting of zinc, chromium, manganese and iron, and X is an anion, and w is an integer which balances the anionic charge of X.

2. The 1:1 L-form transition metal complex salt of claim 1 wherein M is zinc.

3. The 1:1 L-form transition metal complex salt of claim 1 wherein M is manganese.

4. The 1:1 L-form transition metal complex salt of claim 1 wherein M is iron.

5. The 1:1 L-form transition metal complex salt of claim 1 wherein M is chromium.

6. The 1:1 L-form transition metal complex salt of claim 1 wherein X is an organic anion.

7. The 1:1 L-form transition metal complex salt of claim 1 wherein X is an organic monobasic acid anion selected from the group consisting of acetic, propionic and benzoic.

8. A 1:1 L-form transition metal complexed salt of claim 1 wherein X is an inorganic anion.

9. A 1:1 L-form transition metal complexed salt of claim 1 wherein X is an inorganic anion selected from the group consisting of halides, sulfates and phosphates.

* * * * *